United States Patent [19]
Zuech

[11] 3,956,183
[45] May 11, 1976

[54] CATALYSTS FOR PRODUCTION OF CYCLOALKYLAROMATICS

[75] Inventor: Ernest A. Zuech, Bartlesville, Okla.

[73] Assignee: Phillips Petroleum Company, Bartlesville, Okla.

[22] Filed: May 9, 1974

[21] Appl. No.: 468,488

Related U.S. Application Data

[62] Division of Ser. No. 334,386, Feb. 21, 1973, Pat. No. 3,829,514.

[52] U.S. Cl. ................................ 252/441; 252/450; 252/455 R; 252/460
[51] Int. Cl.² .................... B01J 27/06; B01J 29/06; B01J 29/12
[58] Field of Search ............... 252/441, 450, 460; 260/668 B, 671 C

[56] References Cited
UNITED STATES PATENTS

| | | | |
|---|---|---|---|
| 3,055,840 | 9/1962 | Koch, Jr. | 252/460 X |
| 3,084,204 | 4/1963 | Domash et al. | 260/671 C |
| 3,297,564 | 1/1967 | Peck et al. | 252/460 X |

Primary Examiner—Carl F. Dees

[57] ABSTRACT

Cycloalkylaromatics are produced from aromatic hydrocarbons in the presence of hydrogen and an aqueous HF-treated ruthenium halide-active clay catalyst which has been promoted with at least one compound of iron, cobalt, and nickel. Preferably the catalyst has not been heated under calcination conditions prior to use. In a specific embodiment, benzene is converted to cyclohexylbenzene with good selectivity over an active clay impregnated with ruthenium chloride and hydrogen fluoride and at least one compound of iron, cobalt, and nickel.

10 Claims, No Drawings

CATALYSTS FOR PRODUCTION OF CYCLOALKYLAROMATICS

This application is a divisional application of my copending application having Ser. No. 334,386, filed Feb. 21, 1973, now U.S. Pat. No. 3,829,514 entitled "Production of Cycloalkylaromatics."

This invention relates to the conversion of aromatic hydrocarbons to cycloalkylaromatics and/or alkyl-substitited cycloalkylaromatics. In accordance with one aspect, the invention relates to an improved process for and catalyst for conversion of benzene to cyclohexylbenzene over a catalyst comprising an aqueous HF-treated ruthenium-active clay catalyst promoted with at least one compound of iron, cobalt, and nickel. In accordance with a further aspect, this invention relates to an improved catalyst for the conversion of aromatics to cycloalkylaromatics which catalyst has been prepared by impregnation of an active clay with an aqueous solution of HF followed by impregnation with an alcoholic or aqueous solution of a ruthenium halide and halide of one of the metal promoters followed by heating at a temperature below about 380°C to remove solvent but insufficient to subject the catalyst composition to calcination conditions.

Methods are available in the art for the coupling of aromatic nuclei in the presence of molecular hydrogen to produce an at least partially hydrogenated dimer derivative of the aromatic reactant. For example, benzene is converted at elevated temperature to a mixture containing cyclohexylbenzene in the presence of various catalysts. Cyclohexylbenzene is known as a valuable solvent and chemical intermediate. It can be converted in high yield to phenol and cylcohexanone by autooxidation with subsequent acid treatment. None of the prior art methods of producing cyclohexylbenzene have yet been proven for a stable continuous operation necessary for commercial exploitation. Problems therewith include high catalyst cost, catalyst stability and regeneration.

In accordance with the invention there has been discovered a process utilizing an improved ruthenium-clay catalyst which provides not only excellent selectivity for the conversion of aromatics to cycloalkylaromatic hydrocarbons but which is suitable for continuous operation.

Accordingly, an object of the present invention is to provide an improved process for the conversion of aromatic hydrocarbons to cycloalkyl-aromatic hydrocarbons.

Another object of the invention is to provide an improved process and catalyst for the production of cyclohexylbenzene from benzene.

A further object of this invention is to provide an improved ruthenium catalyst exhibiting excellent selectivity for the conversion of benzene to cyclohexylbenzene.

Other objects and aspects, as well as the several advantages of the invention, will be apparent to those skilled in the art upon reading the specification and the appended claims.

In accordance with the invention, a process is provided for producing cycloalkylaromatics and alkyl-substituted cycloalkylaromatics from aromatic hydrocarbons by contacting monocyclic aromatic hydrocarbons or alkyl-substituted monocyclic aromatic hydrocarbons with hydrogen in the presence of an aqueous hydrogen fluoride-treated ruthenium halide-active clay catalyst promoted with at least one compound of iron, cobalt and nickel.

In accordance with one specific embodiment of the invention, a catalyst exhibiting excellent selectivity for the conversion of benzene to cyclohexylbenzene is prepared by impregnating an aqueous HF-treated active clay with an alcoholic or aqueous solution of a ruthenium halide and a halide of at least one of iron, cobalt and nickel, followed by heating to remove solvent under non-calcination conditions.

In accordance with another embodiment of the invention, a catalyst exhibiting excellent selectivity for the conversion of benzene to cyclohexylbenzene is prepared by impregnating an active clay with aqueous hydrofluoric acid prior to impregnation with an aqueous or alcoholic solution of ruthenium halide and at least one of iron, cobalt and nickel.

In a further embodiment of the invention, benzene is converted to cyclohexylbenzene in good selectivity over an aqueous HF-treated ruthenium chloride-active clay catalyst promoted with at least one compound of iron, cobalt or nickel and which catalyst has been prepared by impregnation of the active clay with an alcohol or aqueous solution of ruthenium chloride and the promoting compound followed by heating to remove solvent at a temperature not in excess of about 380°C. The catalyst is preferably used in tablet form although the impregnated powder is suitable. As demonstrated by the specific working examples herein, benzene is converted to cyclohexylbenzene with good selectivity over the inventive catalyst composites.

The feedstocks which are suitable for use in the present invention are aromatic compounds, i.e., monocyclic aromatic hydrocarbons and alkyl-substituted monocyclic aromatic hydrocarbons. Some specific examples of these are benzene, toluene, the xylenes, and the like, and mixtures thereof.

The aromatic conversion according to the invention can be carried out in the presence of the above-described catalyst at temperatures as low as 100°C and under hydrogen pressures as low as 100 psig. The reaction temperature can be as high as 250°C, but it is preferred that no higher than 175°C be employed. Hydrogen pressures not exceeding 1,000 psig are also preferred although hydrogen pressures up to about 2,000 psig can be used. Space velocity defined as volume of the liquid feed per volume of catalyst per hour (LHSV) should be at least 0.5 and not over about 20. However, it is preferable that the LHSV be at least 2 and not above about 15.

The present process is effected in the presence of an aqueous HF-treated clay-supported ruthenium catalyst promoted with at least one compound of iron, cobalt, and/or nickel. The ruthenium and metal promoters are applied to the active clay support material preferably as an alcoholic or aqueous solution of a metal halide salt preferably the chloride.

As indicated above, the support materials for the catalyst of the invention include the montmorillonite clays which preferably have been compacted as by tableting or extrusion. Good results are obtained when an aqueous HF-treated support characterized by montmorillonite structure is impregnated with an alcoholic or aqueous solution of the metal halides, including the promoter metals, followed by heating to remove the solvent. Filtrol Grade 49 clay is an especially good commercially available montmorillonite clay for forming catalysts of this invention. Commercially available extruded montmorillonite clays such as Filtrol Grades 62 and 71 can also be employed.

In summary, the preferred embodiment of the present invention is a process which comprises contacting benzene preferably containing little if any sulfur at a temperature of 110° to 175°C at a LHSV of 2 to 15, and under hydrogen pressure of 200 to 1,000 psig, with a catalyst comprising an aqueous HF-treated clay supported ruthenium catalyst promoted with at least one compound of iron, cobalt, and/or nickel which catalyst has been prepared by impregnating an aqueous HF-treated clay with an alcoholic or aqueous solution of ruthenium halide and a promoter metal halide followed by removal of the solvent by heating under noncalcination conditions at a temperature below about 380°C. Cyclohexylbenzene is recovered from the reaction mixture.

The above montmorillonite clays suitable for this invention are preferably employed in a compacted state although finely divided powders can also be impregnated if desired. The compacted state for montmorillonite clays can be achieved by two general methods which are well known in the art. First, there is a method whereby essentially dry (chemically bound water can be present) powdered clay in the presence of a lubricant such as graphite is formed into tablets, pills, pellets, and the like by conventional means. The second general method involves the use of a slurry, paste or dough of the montmorillonite clay admixed with a volatile liquid, usually water, to form shaped and compacted montmorillonite pellets, or extruded shapes such as cylinders, tubes and the like by conventional means. Regardless of which method is employed, for the purposes of this invention the final compacted montmorillonite clay in the form of a tablet, pellet or the like has a crushing strength of from 3–15, preferably from 5–10, pounds.

A typical analysis of dry Filtrol Grade 71 clay powder suitable for employment in the practice of the present invention is as follows: 71.2% $SiO_2$, 16.5% $Al_2O_3$, 3.6% $Fe_2O_3$, 3.2% MgO, 2.6% CaO, 1.3% $SO_3$, 1.0% ($K_2O$ + $Na_2O$), and 0.6% $TiO_2$ (analysis on a volatile free basis).

Suitable clays are available commercially as, for example, Filtrol Grade 71, Filtrol Grade 62, Filtrol Grade 49, and the like (sold by Filtrol Corporation, Vernon, Cal.). Filtrol Grade 49 and Filtrol Grade 62 clays have the following analysis: 74.0% $SiO_2$, 17.5% $Al_2O_3$, 4.5% MgO, and 1.4% $Fe_2O_3$. Samples of Filtrol Grade 49 and Filtrol Grade 62 were analyzed by the supplier after heating the Filtrol samples at 1700°F. In this heat treatment Filtrols 49 and 62 lost, respectively, 17% and 5% volatiles.

It is presently preferred to contact the active clay as the extrudate or powdered extrudate with aqueous hydrofluoric acid prior to impregnation with an aqueous or an alcoholic solution of ruthenium halide and the promoter metal halides. Alternatively, the active clay can be contacted with an aqueous solution containing hydrofluoric acid, promoter halide and ruthenium halide. If desired, the active clay can be converted to tablets before the aqueous HF treatment. Extrudate or powdered extrudate can be HF treated, impregnated, dried and used as a catalyst or the dried, impregnated powder can be converted to tablets before use.

Following impregnation of the HF-treated active clay with a solution of the ruthenium halide and promoter metal halide salts, the solvent can be removed in vacuo at ambient temperatures, say, about 25°C. The impregnated clay can be further dried by heating at temperatures in the range 110°–120°C although temperatures up to 380°C can be used. The heating is continued for a period of time and under conditions sufficient to remove substantially all of the solvent but insufficient to calcine the catalyst composition.

The HF-treated ruthenium-active clay catalyst promoted with a compound of iron, cobalt, and nickel, and mixtures thereof, will contain generally from about 0.01 to 2 weight percent, and preferably 0.1 to 1 weight percent, ruthenium. The amount of metal promoter present in the catalyst will generally be in the range of 0.001 to 3 weight percent, preferably 0.05 to 1 weight percent, iron, cobalt, or nickel. The weight ratio of ruthenium to metal promoter (nickel, cobalt or iron) will be in the range 10:1 to 1:1.5, preferably 1:0.5 to 1:1. The amount of HF employed will be in the range of 1 to 15 weight percent, preferably 5 to 10 weight percent, based on the weight of active clay.

The present invention is advantageously practiced under substantially anhydrous conditions and can be carried out in a batchwise, semi-continuous or continuous operation. However, continuous operation is more suitable for commercial utilization. In a continuous process, the aromatic hydrocarbon-hydrogen feed can be passed over the fixed bed catalyst in an upflow or downflow manner.

The reaction can be conducted in the presence of or in the substantial absence of added reaction solvents or diluents. In the modification wherein added solvent is employed, the solvents which are liquid at reaction temperature and pressure and are inert to the catalyst, reactants and reaction products are suitably employed. Preferred solvents to be utilized in this modification are saturated hydrocarbons of from 6–16 carbon atoms, e.g., acyclic alkanes such as hexane, decane, octane, dodecane, and hexadecane, as well as cycloalkanes such as cyclohexane, cyclooctane, cyclododecane, and decahydronaphthalene.

The operability of the present invention is shown by Examples I–VII (corresponding to runs 1–7 in Table I) using Filtrol Grade-49 as the support.

SPECIFIC EXAMPLES

A. Catalyst Preparation (Control Run)

A 22.0 g portion of Filtrol Grade 49 in a 100 ml round bottomed flask was treated with a solution of 0.14 g ruthenium trichloride and 0.22 g nickel(II) chloride hexahydrate in 40 ml ethanol. The ethanol was removed at reduced pressure on a rotary evaporator. The residual material was transferred to a 500 ml round bottomed flask, and the 100 ml round bottomed flask rinsed with two 25 ml portions of ethanol. These ethanol washings were combined with the residual particles in the 500 ml round bottomed flask and the ethanol was removed under reduced pressure on a rotary evaporator. The residue was used as a catalyst.

B. Cyclohexylbenzene (Control Run)

A charge of 30 ml (23.9 g) of the above catalyst (0.25% Ru, 0.25% Ni) was placed in a ½-inch I.D. upflow tube reactor bedded with 30 ml of 3 mm glass beads and the catalyst was covered with 4 mm glass beads. The system was pressure checked, heated to 150°C, pressured to 500 psig $H_2$ and benzene was pumped in at a rate of 120 ml/hr with a slight hydrogen flow during a reaction period of approximately 8 hours. The reactor effluent was collected in a receiver which was changed at approximately 1-hour intervals, and the composition of each sample was determined by glc analysis. The glc analyses of samples taken during the last 4 hours of the run were averaged and the results showed an 18.2% conversion based on benzene with a selectivity of 18% to cyclohexane and 67% to cyclohexylbenzene.

EXAMPLE I

A. Catalyst Preparation

A 25 g portion of Filtrol Grade 49 was treated with a solution containing 2.5 g of 50% hydrofluoric acid and 70 ml of water. The mixture was allowed to stand 15 minutes at room temperature, and the water was removed under reduced pressure on a rotary evaporator. The residue was treated with a solution of 0.17 g ruthenium trichloride and 0.25 g nickel(II) chloride hexahydrate in 50 ml ethanol. The ethanol was removed under reduced pressure on a rotary evaporator.

B. Cyclohexylbenzene (Run 1)

A charge of 30 ml (25.35 g) of the above catalyst [0.25% Ru, 0.25% Ni from ethanol on HF-treated Filtrol Grade 49 (5 wt. % HF/Filtrol)] was placed in a ½-inch I.D. upflow tube reactor bedded with 30 ml of 3 mm glass beads and the catalyst was covered with 4 mm glass beads. The reaction was carried out in the same manner as the control run for a period of approximately 8 hours. The glc analyses of samples taken during the last 3⅔ hours of the run were averaged and the results showed 13% conversion based on benzene with a selectivity of 13% to cyclohexane and 73% to cyclohexylbenzene.

EXAMPLE II

A. Catalyst Preparation

The catalyst was prepared as described in Example I except that an aqueous rather than an ethanolic solution of ruthenium trichloride and nickel(II) chloride hexahydrate was used.

B. Cyclohexylbenzene (Run 2)

This run was carried out in the same reactor and under approximately the same conditions as the control run for a period of about 8 hours. A 30 ml (22.6 g) portion of the above catalyst [0.25% Ru, 0.25% Ni from water on HF-treated Filtrol Grade 49 (5 wt. % HF/Filtrol)] was used in this run and also in Run 3 of Example III. The glc analyses of samples taken during the last 4⅔ hours of the run were averaged and the results showed 13% conversion based on benzene with a selectivity of 15% to cyclohexane and 74% to cyclohexylbenzene.

EXAMPLE III (Run 3)

The catalyst bed of Example II was used in this run and other parameters remained the same except the benzene was pumped in at 180 ml/hr rather than 120 ml/hr. The glc analyses of samples taken during the last 5 hours of the run were averaged and the results showed 10% conversion based on benzene with a selectivity of 16% to cyclohexane and 75% to cyclohexylbenzene.

EXAMPLE IV

A. Catalyst Preparation

A solution was prepared which contained 0.20 g ruthenium trichloride, 0.30 g nickel(II) chloride hexahydrate, 50 ml of water, and 3.0 g of 50% hydrofluoric acid. A 30 g sample of Filtrol Grade 49 was treated with the above solution and the water was removed at reduced pressure on a rotary evaporator.

B. Cyclohexylbenzene (Run 4)

This run was carried out using the above catalyst [0.25% Ru, 0.25% Ni from water on HF-treated Filtrol Grade 49 (5 wt. % HF/Filtrol)] for a period of about 7 hours. The glc analyses of samples taken during the last 2⅓ hours of the run showed 10% conversion based on benzene with a selectivity of 15% to cyclohexane and 73% to cyclohexylbenzene.

EXAMPLE V

A. Catalyst Preparation

A 30 g sample of Filtrol Grade 49 was allowed to stand for 30 minutes in a mixture of 40 ml water and 6.0 g of 50% hydrofluoric acid. The water was removed under reduced pressure on a rotary evaporator. The residue was treated with a solution of 0.20 g ruthenium chloride and 0.30 g nickel(II) chloride hexahydrate in 40 ml ethanol. The ethanol was removed under reduced pressure on a rotary evaporator.

B. Cyclohexylbenzene (Run 5)

This run was carried out using the above catalyst [0.25% Ru, 0.25% Ni from ethanol on HF-treated Filtrol Grade 49 (10 wt.% HF/Filtrol) ] for a period of about 8 hours. The same reactor and approximately the same reaction conditions were used as employed in the control run. The glc analyses of samples taken during the last 5 hours of the run showed 16% conversion based on benzene with a selectivity of 15% to cylcohexane and 70% to cyclohexylbenzene.

EXAMPLE VI

A. Catalyst Preparation

A 30 g sample of Filtrol Grade 49 was contacted with a mixture of 70 ml water and 3.0 g of 50% hydrofluoric acid for a period of 15 minutes. The water was removed under reduced pressure on a rotary evaporator. The residual material was treated with 0.121 g ruthenium trichloride and 0.181 g nickel(II) chloride hexahydrate in 50 ml ethanol. The ethanol was removed under reduced pressure on a rotary evaporator.

B. Cyclohexylbenzene (Run 6)

A charge of 30 ml (24.6 g) of the above catalyst [0.15% Ru, 0.15% Ni from ethanol on HF-treated Filtrol Grade 49 (5 wt.% HF/Filtrol)] was placed in a tube reactor bedded with 30 ml of 3 mm glass beads. This run was carried out for a period of about 8 hours under approximately the same conditions cited in the control run. The glc analyses of samples taken during the last 5 hours of the run were averaged and showed 10% conversion based on benzene with a selectivity of 16% to cyclohexane and 74% to cyclohexylbenzene.

EXAMPLE VII (Run 7)

Thus run was carried out for 8 hours over the catalyst bed of Example VI but at 140°C rather than 150°C. The glc analyses of samples taken during the last 6 hours of the run were averaged and showed 8% conversion based on benzene with 17% selectivity to cyclohexane and 76% to cyclohexylbenzene.

EXAMPLE VIII

A. Catalyst Preparation

A 60 g portion of Filtrol Grade 49 was treated with a solution containing 24 g of 50% hydrofluoric acid and 75 ml water. The mixture was allowed to stand 1.5 hours, and the water was removed under reduced pressure on a rotary evaporator. The residue was treated with a solution of 0.17 g ruthenium trichloride and 0.25 g nickel(II) chloride hexahydrate in 50 ml ethanol. The ethanol was removed under reduced pressure on a rotary evaporator.

B. Cyclohexylbenzene (Control Run)

A charge of 30 ml (25.5 g) of the above catalyst [0.25% Ru, 0.25 % Ni from ethanol on HF-treated Filtrol 49 (20 wt. % HF/Filtrol)] was placed in a ½-inch I.D. upflow tube reactor bedded with 30 ml of 3 mm glass beads and the catalyst was covered with 4 mm glass beads. The reaction was carried out in a manner comparable to the control run of Table I for a period of 8 hours. The glc analyses indicated poorer selectivity to cyclohexylbenzene of this system (cyclohexylbenzene/cyclohexane ratio was 0.7) relative to runs 1–7 of Table I.

EXAMPLE IX

A. Catalyst Preparation

A 30 g sample of Filtrol Grade 49 was contacted for 30 minutes with a mixture of 40 ml water and 6 g of 50% hydrofluoric acid. The water was removed under reduced pressure on a rotary evaporator. The residue was treated with a solution of 0.20 g ruthenium trichloride and 0.60 g nickel(II) chloride hexahydrate in 40 ml ethanol. The ethanol was removed under reduced pressure on a rotary evaporator.

B. Cyclohexylbenzene (Control Run)

This run was carried out for a period of 8 hours using the above catalyst [0.25% Ru, 0.5% Ni from ethanol on HF-treated Filtrol Grade 49 (10 wt. % HF/Filtrol)]. This run was carried out in a manner comparable to the above control run. The glc analyses of samples taken during the last 5 hours of the run were averaged and showed 14% conversion based on benzene with 20% selectivity to cyclohexane and 68% to cyclohexylbenzene.

It will be observed from this example that as the amount of metal promoter (Ni) is increased to a Ru/Ni ratio of 1:2 that selectivity decreases (cyclohexylbenzene/cyclohexane ratio was 3.35) in comparison with Runs 1–7 in Table I where the ratio of Ru/Ni was 1:1.

EXAMPLE X

A. Catalyst Preparation

A 45 ml sample of Filtrol Grade 49 was treated with a 3:1 stream of helium:anhydrous HF (HF 40 ml/min) for a period of 30 minutes. The HF-treated Filtrol Grade 49 was then contacted with 0.17 g ruthenium trichloride and 0.25 g nickel(II) chloride hexahydrate in 40 ml ethanol. The ethanol was removed under reduced pressure on a rotary evaporator.

B. Cyclohexylbenzene (Control Run)

This run was carried out for a period of approximately 8 hours over the above catalyst (0.25% Ru, 0.25% Ni from ethanol on anhydrous HF-treated Filtrol Grade 49). This run was carried out in a manner comparable to the control run. The glc analyses of samples taken during the last 4 hours of the run showed 17% conversion based on benzene with a 22% selectivity to cylcohexane and 64% to cyclohexylbenzene (cyclohexylbenzene/cyclohexane ratio was 2.9).

This run demonstrates that selectivity decreases when the catalyst is treated with anhydrous HF (note cyclohexylbenzene/cyclohexane ratios in Runs 1–7 in Table I).

TABLE I

Cyclohexylbenzene from Benzene/$H_2$ over HF-Treated Filtrol 49 Catalysts

| Run No. | Metals on Filtrol 49 | Catalyst Preparation | $C_6H_{12}$ | $C_6H_6$ | Unknown | Products, Weight Percent MeCpBz No. | CyBz No. | Heavies+ | CyBz/$C_6H_{12}$ | Selectivity CyBz % |
|---|---|---|---|---|---|---|---|---|---|---|
| Control | 0.25% Ru, 0.25% Ni | (a) | 3.2 | 81.8 | 0.1 | 0.1 | 12.2 | 2.6 | 3.7 | 67 |
| 1 | 0.25% Ru, 0.25% Ni | (b) | 2.0 | 85.1 | 0.05 | 0.1 | 10.9 | 1.9 | 5.6 | 73 |
| 2 | 0.25% Ru, 0.25% Ni | (c) | 2.1 | 86.1 | Trace | 0.15 | 10.3 | 1.3 | 4.9 | 74 |
| 3* | 0.25% Ru, 0.25% Ni | (c) | 1.8 | 89.1 | Trace | 0.1 | 8.2 | 0.8 | 4.6 | 75 |
| 4 | 0.25% Ru, 0.25% Ni | (d) | 1.8 | 88.1 | Trace | 0.1 | 8.7 | 1.3 | 4.8 | 73 |
| 5 | 0.25% Ru, 0.25% Ni | (e) | 2.8 | 81.5 | 0.1 | 0.3 | 12.9 | 2.5 | 4.6 | 70 |
| 6 | 0.15% Ru, 0.15% Ni | (b) | 1.7 | 89.3 | 0.05 | 0.1 | 7.9 | 0.9 | 4.65 | 74 |
| 7 | 0.15% Ru, 0.15% Ni | (b) | 1.4 | 91.6 | Trace | 0.1 | 6.4 | 0.5 | 4.55 | 76 |

No. McCpBz and CyBz represent, respectively, methylcyclopentylbenzene and cyclohexylbenzene.
+Heavies were estimated by determining the residue remaining after distillation, and normalization of the glc data.
*LHSV = 6. The LHSV is 4 in the other runs.
(a) Filtrol 49 was not treated with HF; Ru and Ni were added from ethanol solution as $RuCl_3$ and $NiCl_2$.
(b) 5 weight percent HF based on Filtrol 49 was added to Filtrol 49 from water solution; Ru and Ni were added from ethanol solution as $RuCl_3$ and $NiCl_2$.
(c) Same as (b) except Ru and Ni were added from water solution as $RuCl_3$ and $NiCl_2$.
(d) A water solution of $RuCl_3/NiCl_2$/HF was contacted with Filtrol 49 (5 wt. percent HF based on Filtrol 49).
(e) Same as (b) except 10 weight percent HF based on Filtrol 49 was added to Filtrol 49 from water solution.

The cyclohexylbenzene/cyclohexane ratios of runs 1–7 in Table I indicate the greater selectivity to cyclohexylbenzene of the inventive runs employing aqueous HF-treated catalytic systems as opposed to the untreated catalyst system of the control run.

The heavies produced in the present inventive cyclohexylbenzene process can be equilibrated with benzene in the presence of a Lewis acid such as aluminum chloride to increase the yield of the desired cyclohexylbenzene. The major by-product components (75 weight percent of the heavies) produced in the inventive process are polycycloalkylaromatics such as dicyclohexylbenzenes and tricyclohexylbenzenes. As is well known in the art, the transalkylation of polycycloalkylaromatics with aromatics can be effected in the presence of acid catalysts such as aluminum chloride, ferric chloride, zinc chloride, boron trifluoride, stannic chloride, polyphosphoric acid, hydrogen fluoride, antimony pentafluoride, and the like. Alternatively, heterogeneous catalysts such as active clays, zeolites, supported phosphoric acid, fluorided alumina, and the like can also be used.

I claim:

1. A process for the preparation of a promoted ruthenium halide-active clay catalyst which comprises the steps of treating a particulate active clay with aqueous HF followed by impregnation with an alcoholic or aqueous solution of a ruthenium halide and a halide of at least one of iron, cobalt, or nickel, and removing the alcohol or water from the impregnated catalyst by heating at a temperature sufficient to volatilize said alcohol or water, and remove same from said catalyst but insufficient to calcine the catalyst composition.

2. A process according to claim 1 wherein said ruthenium halide is ruthenium trichloride and said solvent is ethanol and said heating is effected at a temperature below about 380°C.

3. A process according to claim 1 wherein the amount of ruthenium deposited on said active clay is in the range of 0.01 to 2 weight percent, the amount of metal promoter is in the range of 0.001 to 3 weight percent, the amount of HF based on active clay is in the range of 1 to 15 weight percent, and the weight ratio of ruthenium to metal promoter is in the range of 10:1 to 1:1.5.

4. A process according to claim 1 wherein aqueous HF is applied to the active clay followed by heating to remove water therefrom and then the HF-treated active clay is impregnated with an ethanolic solution of ruthenium trichloride and metal promoter chloride followed by heating to remove alcohol therefrom under conditions insufficient to calcine said catalyst composite.

5. A process according to claim 1 wherein the ruthenium halide-active clay catalyst is a ruthenium chloride-montmorillonite active clay catalyst promoted with nickel which has been treated with 1 to 15 weight percent HF based on active clay.

6. An active clay-ruthenium halide non-calcined catalyst composition effective for the conversion of aromatics to cycloalkylaromatics comprising 0.01 to about 2 weight percent ruthenium promoted with from 0.001 to about 3 weight percent of at least one promoter metal halide compound of iron, cobalt, and nickel in a weight ratio of ruthenium to promoter metal in the range 10:1 to 1:1.5 and which catalyst has been treated with aqueous HF in an amount ranging from 1 to 15 weight percent based on active clay.

7. A catalyst according to claim 6 wherein said catalyst is a ruthenium chloride-montmorillonite active clay.

8. A catalyst according to claim 6 wherein the promoter metal is nickel.

9. A catalyst according to claim 6 wherein the catalyst contains from 0.1 to 1 weight percent ruthenium, 0.05 to 1 weight percent promoter metal, the weight ratio of ruthenium to promoter metal is 1:0.5 to 1:1, and the amount of HF present, based on active clay, is 5 to 10 weight percent.

10. A catalyst according to claim 7 wherein the promoter metal is nickel.

* * * * *